(12) United States Patent
Arinaga et al.

(10) Patent No.: US 8,445,262 B2
(45) Date of Patent: May 21, 2013

(54) METHOD FOR EVALUATING ANALYTE

(75) Inventors: Kenji Arinaga, Kawasaki (JP); Ulrich Rant, Munich (DE); Simon Scherer, Westheim (DE); Erika Pringsheim, Munich (DE)

(73) Assignee: Fujitsu Limited, Kawasaki (JP)

( * ) Notice: Subject to any disclaimer, the term of this patent is extended or adjusted under 35 U.S.C. 154(b) by 249 days.

(21) Appl. No.: 12/239,987

(22) Filed: Sep. 29, 2008

(65) Prior Publication Data

US 2009/0130777 A1 May 21, 2009

(30) Foreign Application Priority Data

Sep. 27, 2007 (JP) ................................. 2007-252542

(51) Int. Cl.
*C12M 1/34* (2006.01)
*C12M 3/00* (2006.01)

(52) U.S. Cl.
USPC ......... 435/287.1; 436/164; 436/172; 435/7.1; 435/283.1; 435/287.2; 435/288.7; 422/82.05; 422/82.08

(58) Field of Classification Search
USPC ............. 436/164, 172; 435/7.1, 283.1, 287.1, 435/287.2, 288.7; 422/82.05, 82.08
See application file for complete search history.

(56) References Cited

U.S. PATENT DOCUMENTS

| | | | |
|---|---|---|---|
| 6,835,552 B2 * | 12/2004 | Miles et al. | 435/7.32 |
| 2004/0202577 A1 * | 10/2004 | McNeil et al. | 422/82.08 |
| 2005/0069932 A1 | 3/2005 | Arinaga et al. | |
| 2005/0194250 A1 * | 9/2005 | Frey et al. | 204/403.01 |
| 2005/0221387 A1 * | 10/2005 | Jibu | 435/7.1 |
| 2007/0128615 A1 * | 6/2007 | Su | 435/6 |

FOREIGN PATENT DOCUMENTS

| | | |
|---|---|---|
| EP | 1901057 A1 | 3/2008 |
| JP | 2005-283560 A | 10/2005 |
| JP | 2007-139468 A | 6/2007 |
| WO | 2007/007519 A1 | 1/2007 |

OTHER PUBLICATIONS

T. G. Drummond et al., "Electrochemical DNA sensors", Nature Biotech, Oct. 2003, pp. 1192-1199, vol. 21, No. 10.
J. Wang, "Survey and Summary From DNA biosensors to gene chips", Nucleic Acids Reseach, 2000, pp. 3011-3016, vol. 28, No. 16.
U. Rant et al., "Dynamic Electrical Switching of DNA Layers on a Metal Surface", Nano Letters, 2004, pp. 2441-2445, vol. 4, No. 12.
A. Ulman, "Formation and Structure of Self-Assembled Monolayers", Chem. Rev., 1996, pp. 1533-1554, vol. 96.

(Continued)

*Primary Examiner* — Melanie Y Brown
(74) *Attorney, Agent, or Firm* — Westerman, Hattori, Daniels & Adrian, LLP

(57) ABSTRACT

In an analyte evaluation method for evaluating an analyte, AC voltage is applied between a substrate electrode on a substrate and a counter electrode, and signals obtained from a marker provided on an analyte bound to the substrate electrode are observed, wherein the frequency of the AC voltage is changed and the behavior of the average value of the marker signals is observed. A novel, highly-selective, low-noise method of evaluating a object of evaluation is thus achieved.

16 Claims, 8 Drawing Sheets

OTHER PUBLICATIONS

U. Rant et al., "Dissimilar Kinetic Behavior of Electrically Manipulated Single- and Double-Stranded DNA Tethered to a Gold Surface", Biophysical Journal, May 2006, pp. 3666-3671, vol. 90.

European Search Report dated Nov. 23, 2009, issued in corresponding European Patent Application No. 08165274.5.

European Office Action dated Oct. 26, 2010, issued in corresponding European Patent Application No. 08165274.5.

European Office Action dated Oct. 19, 2011, issued in corresponding European Patent Application No. 08165274.5.

Japanese Office Action dated Nov. 13, 2012, issued in corresponding Japanese Patent Application No. 2007-252542, (4 pages) With English Translation.

* cited by examiner

Fluorescent dye Cy3

Methylene blue

Ferrocene

Digoxigenin

METHOD FOR EVALUATING ANALYTE

CROSS-REFERENCE TO RELATED APPLICATIONS

This application is based upon and claims the benefit of priority from the prior Japanese Patent Application No. 2007-252542, filed on Sep. 27, 2007, the entire contents of which are incorporated herein by reference.

TECHNICAL FIELD

The following embodiments relate to a method for evaluating an object of evaluation.

BACKGROUND

In recent years, much interest has focused on the field of nanotechnology or "nano" as it is known.

In the field of nanotechnology, research and development is particularly active in the area of nano-biotechnology, which is a new field that merges semiconductor nanotechnology and biotechnology, as it may provide fundamental solutions to existing problems.

In this area of nano-biotechnology, DNA chips (or DNA microarrays) and other biochips, in which multiple different analytes of DNA, proteins or other biopolymers are spotted in high-density arrays on substrates formed of glass, silicon, plastic, metal and the like, are of interest as a way of simplifying nucleic acid and protein testing in the fields of clinical diagnosis, drug therapy and the like, and particularly an effective tool for gene analysis (T. G. Drummond et al., "Electrochemical DNA sensors", Nature Biotech., 2003, Vol. 21, No. 10, p. 1192-1199; J. Wang, "Survey and summary from DNA biosensors to gene chips", Nucleic Acids Research, 2000, Vol. 28, No. 16, p. 3011-3016).

In recent years, attention has focused on devices called "MEMS" and "μTAS", which are prepared based on a technology for evaluating extremely small targets in which a functional molecule or a molecule bound to a functional molecule is bound to part of a solid substrate to form a functional surface (evaluation part), in combination with micromachining techniques and microsensing techniques, because they offer great improvements over conventional evaluation sensitivity and evaluation time. "MEMS" is an abbreviation for micro-electro mechanical systems, and signifies a technology for producing extremely small systems with semiconductor processing technology or a precise micro-machine prepared using this technology, or more generally a system in which the mechanical, optical, fluid and other functional parts are integrated and miniaturized. "μTAS" is an abbreviation for micro total analysis system, and signifies a small-scale, integrated analysis system of micropumps, microvalves, sensors and the like. These devices generally have functional surfaces with functional molecules having specific functions, or molecules bound to such functional molecules, fixed (bound) by self-organization on a substrate. Many methods are used for electrically or optically evaluating reactions on the functional surfaces of these devices.

Of these, optical evaluation methods are methods in which a target (object of evaluation) is modified with a fluorescent dye or other optical label, and is then evaluated quantitatively according to the optical intensity, and these methods are widely used in DNA chips and the like because of their high sensitivity.

However, these methods require a procedure of modifying the target with a label, and require complex steps such as labeling, washing and the like. Other problems include mis-detection due to contamination by the unattached label, and evaluation of targets adsorbed non-specifically to the evaluation part rather than by specific binding with the probe.

Consequently, there is demand for development of highly selective, low-noise evaluation techniques that do not require the target to be labeled (non-label techniques), and that avoid mis-detection of non-specifically adsorbed targets and the like.

As a label-free method of evaluating a target molecule, a method is known in which a charged analyte is labeled with a marker, the analyte is fixed on an electrode and driven with an electric field, the motion of the analyte is monitored according to the signal from the marker, the motion of the analyte changes when the target molecule has bound specifically to the analyte, and this change is evaluated by means of the marker modifying the analyte (U. Rant et al., "Dynamic electrical switching of DNA layers on a metal surface", Nano Lett., 2004, Vol. 4, No. 12, p. 2441-2445; Japanese Patent Application No. 2004-238696 (claims); U.S. Patent Application Publication No. 2005069932, claims). The principle is that the charged analyte is attracted to or repelled from the substrate surface by applied electric field, changing the distance between the substrate and the marker attached to the tip of the analyte, and resulting in changes in the signal from the marker that can be observed. As long as the driving frequency is in a frequency range (about 1 MHz or less) that allows formation of an electrical double layer as a source for the electric field, a target molecule can be evaluated by observing the signal from the marker, which is synchronized with the driving potential.

SUMMARY

One mode of the embodiments provides an analyte evaluation method for evaluating an analyte by applying AC voltage between a substrate electrode on a substrate and a counter electrode, and observing a signal obtained from a marker provided on an analyte bound to the substrate electrode, wherein the frequency of the AC voltage is changed and the behavior of the average value of the marker signals is observed.

BRIEF DESCRIPTION OF THE DRAWINGS

FIG. 1-B is a schematic view showing the behavior of an analyte;

FIG. 1-C is a schematic view showing the behavior of an analyte;

DESCRIPTION OF THE EMBODIMENTS

Figure 1A:
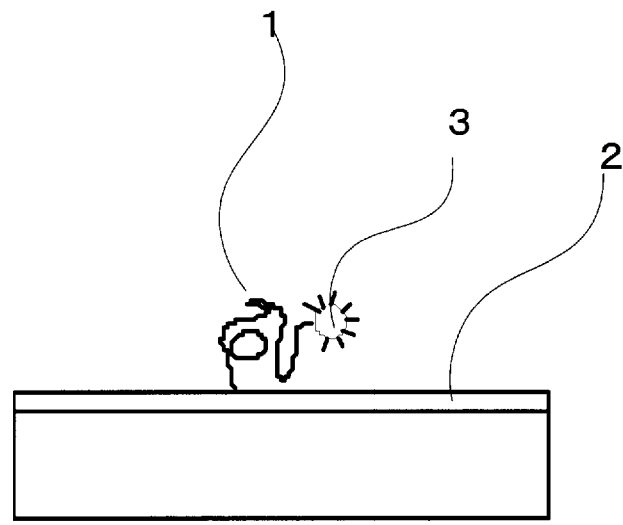
FIG. 1-A is a schematic view showing the behavior of an analyte.

Embodiments are explained below using drawings, examples and the like. These drawings, examples and the like and explanations are meant to illustrate the embodiments, and not to limit its scope. Other embodiments may of course be included in the scope of the embodiments to the extent that they match its intent.

In the analyte evaluation method of the embodiments, AC voltage is applied between a substrate electrode on a substrate and a counter electrode, and an analyte is evaluated by observing signals obtained from a marker attached on an analyte bound to the substrate electrode. This is done by changing the frequency of the AC voltage and observing the behavior of the average value of the marker signals. The frequency of the AC voltage is sometimes called a driving frequency because it causes the movement (such as elongation and contraction) of the analyte that in turn is the origin of the marker signal behavior, and causing such movement of the analyte is sometimes called driving the analyte.

A method of evaluating an analyte by applying AC voltage between a substrate electrode on a substrate and a counter electrode and observing signals obtained from a marker attached on an analyte bound to the electrode is disclosed for example in Japanese Patent Application Laid-open No. 2005-283560 (claims).

The method of the embodiments allows a novel evaluation of an object of evaluation with high selectivity and low noise. Specifically, an evaluation method is achieved which does not require the object of evaluation to be modified with a marker, thereby avoiding the undesirable effects that result if any amount of residual marker remains from the evaluation marker used to modify the object of evaluation, as well as mis-detection of non-specifically adsorbed target and the like.

The highly-selective, low-noise molecule evaluation method and evaluation apparatus of the embodiments are extremely useful in the field of nano-biotechnology, and can provide an evaluation method and evaluation apparatus using this method that are suited to DNA chips, protein chips and other biochips. Here, the "evaluation" signifies to detect the presence or absence an evaluation object, to identify the similarity and difference, and/or to determine the quantity of the evaluation object.

(Analyte Evaluation Apparatus)

In the aforementioned analyte evaluation method, evaluation can be accomplished using an analyte evaluation apparatus comprising a substrate electrode on a substrate, a counter electrode, an analyte that binds to the substrate electrode and is provided with a marker, a voltage application means for applying voltage between the substrate electrode and the counter electrode, and a signal detection means for detecting a signal from the marker. The signal detection means may include an auxiliary means such as a fluorescence-emitting means for causing emission and quenching of fluorescence in the case of a fluorescence detection means. The substrate electrode and counter electrode are used immersed in an aqueous solution.

The explanation below mainly pertains to cases involving observation of the emission and quenching of fluorescence from a marker, but as discussed below, the signal in the embodiments need not be a fluorescent signal.

In this apparatus, the analyte is bound to the substrate electrode, the marker is put in a quenched state by means of the quenching effect, voltage is applied to cause emission and quenching of the marker, and an object of evaluation is evaluated by observing this emission and quenching behavior. It is believed that the emission and quenching of the marker is made possible by changes in the distance between the marker and the substrate electrode. The marker emits when it is farther from the substrate electrode, and quenches when it is close to or in contact with the substrate electrode. It is thought that this behavior of the marker is possible because the analyte can have a positive or negative charge. For example, when the analyte has a minus charge the marker moves away from the substrate electrode when the substrate electrode is given a negative potential, and approaches the substrate electrode when the substrate electrode is given a positive potential.

Figure 1B:
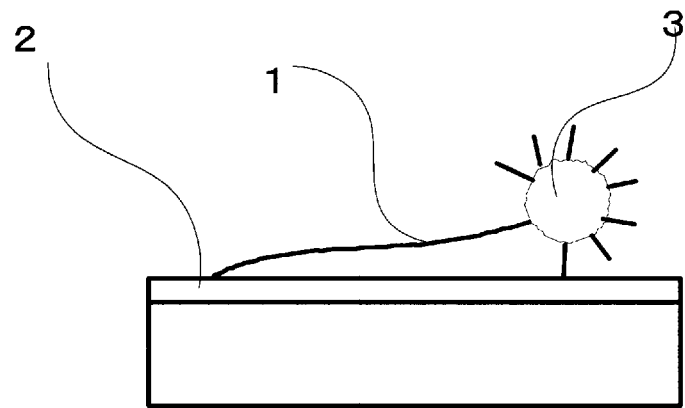
Figure 1C:
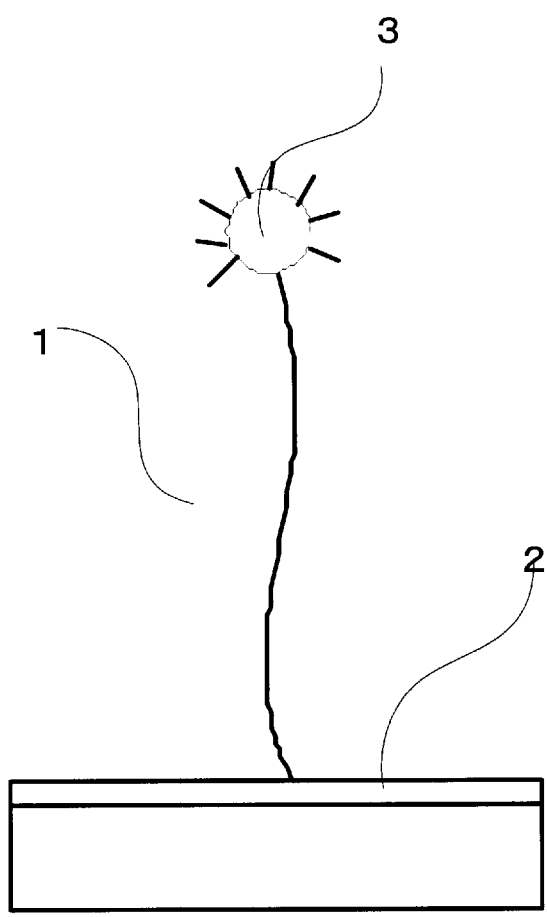

This behavior is shown graphically in FIGS. 1-A through 1-C. FIG. 1-A is a schematic view showing analyte 1 bound to substrate electrode 2 in a contracted state, while FIG. 1-B is a schematic view showing analyte 1 bound to substrate electrode 2 in a horizontally prostrated state, and FIG. 1-C is a schematic view showing analyte 1 extending away from substrate electrode 2. In FIGS. 1-A and 1-B, marker 3 is close to or in contact with the substrate electrode, while in FIG. 1-C the marker 3 is distant from the substrate electrode. This is the behavior that is thought to occur. In this description, references to "elongation and contraction" of the analyte refer to the "elongation and contraction" behavior shown in FIGS. 1-A through 1-C, but any behavior that causes a change in the distance between the marker and substrate electrode is considered to be "elongation and contraction" in this sense. That is, "elongation and contraction" is not limited to the aforementioned behavior.

(Object of Evaluation)

The object of evaluation may be the analyte itself, or may be a substance bound to or capable of binding to the analyte as explained below. When the object of evaluation is bound to or capable of binding with the analyte, the "analyte" and "object of evaluation" may be called the "probe molecule" and "target molecule", respectively. If evaluation is carried out without binding a target molecule to a probe molecule, then the object of evaluation is the analyte itself. "Evaluating the object of evaluation" may mean detecting the presence or absence of, detecting differences in and/or evaluating the amount of the probe molecule, or detecting the presence or absence of, detecting differences in and/or evaluating the amount of the target molecule.

The object of evaluation is preferably selected from or includes one selected from the group consisting of proteins, DNA, RNA, antibodies, natural or artificial single-stranded nucleotide bodies, natural or artificial double-stranded nucleotide bodies, aptamers, products obtained by limited digestion of antibodies with proteases, organic compounds having affinity for proteins, biopolymers having affinity for proteins, complexes of these and any combinations of these. It may also include positively or negatively charged ionic polymer. In the embodiments, examples of the aforementioned complexes include combinations of the aforementioned substance with another substance, such as a combination of DNA with a negatively charged polymer. In addition to those mentioned above, the object of evaluation may be a serum protein, tumor marker, apoprotein, virus, auto-antibody, coagulation and fibrinolysis factor, hormone, drug in blood, nucleic acid, HLA antigen, lipoprotein, glycoprotein, polypeptide, lipid, polysaccharide, lipopolysaccharides or the like.

In the embodiments, a "nucleotide body" is any one selected from the group consisting of mononucleotides, oligonucleotides and polynucleotides, or a mixture of these. Such substances often have a negative charge. They can be used as single strands or double strands. Proteins, DNA and nucleotide bodies may also be mixed together. Biopolymers include not only those from living bodies but also those from living bodies that have been processed, and synthetic molecules.

The aforementioned "product" is obtained by limited digestion of an antibody with a protease, and as long as it matches the intent of the embodiments, may be either an antibody Fab fragment or (Fab)$_2$ fragment, a fragment derived from a Fab fragment or (Fab)$_2$ fragment, or a derivative thereof or the like.

A monoclonal immunoglobulin IgG antibody for example can be used as an antibody. Alternatively, a Fab fragment or (Fab)$_2$ fragment of an IgG antibody can be used as a fragment derived from an IgG antibody. A fragment derived from such a Fab fragment or (Fab)$_2$ fragment may also be used. Examples of organic compounds having affinity for proteins that can be used include nicotinamide adenine dinucleotide (NAD) and other enzyme substrate analogs and enzyme activity inhibitors, neurotransmission inhibitors (antagonists) and the like. Examples of biopolymers having affinity for proteins include proteins that serve as substrates or catalysts for proteins, and constituent proteins of molecular complexes and the like.

(Analyte)

The analyte may be any capable of binding to the substrate electrode to the extent that the intent of the invention is not violated, but the marker is preferably provided before binding with the "target molecule".

The analyte is preferably one having the property of binding specifically as a "probe molecule" to a "target molecule". Because it has the property of binding specifically, highly-selective, low-noise precise evaluation of an object of evaluation as the "target molecule" or of an object of evaluation including both a "target molecule" and a "probe molecule" can be accomplished more easily. The type of binding and the binding location are not particularly limited, but binding with particularly weak binding force should be avoided.

The analyte is normally one having the function of changing the distance between the marker and substrate electrode when subjected to AC voltage. As discussed above, the analyte is preferably one that can take a positive or negative charge so as to cause changes in distance between the marker and substrate electrode when subjected to AC voltage. This kind of analyte is sometimes called a charged analyte.

The shape of the analyte is not particularly limited and can be selected appropriately according to the object, but examples include strands, particles, plates and mixtures of two or more of these and the like. Of these, a strand shape is preferred.

The type of such an analyte is not particularly limited and can be selected appropriately according to the object, but desirable examples include biological molecules and the like for purposes of application to disease medical treatment and diagnosis and the like. Specifically, it preferably includes at least one substance selected from the group consisting of proteins, DNA, RNA, antibodies, natural or artificial single-stranded nucleotide bodies, natural or artificial double-stranded nucleotide bodies, aptamers, products obtained by limited digestion of antibodies with proteases, organic compounds having affinity for proteins, biopolymers having affinity for proteins, complexes of these, positively or negatively charged ionic polymers and any combinations of these. This is because these are often easy to elongate and contract and are also easy to bind specifically as probe molecules to target molecules.

Examples of positively charged ionic polymers include DNA that has been positively charged by binding of guanidine to the main chain (guanidine DNA) and polyamine, or the like. Desirable examples of negatively charged ionic polymers include negatively charged natural nucleotide bodies, polynucleotides, polyphosphoric acid and the like. One kind alone may be used, or two or more kinds may be used in combination.

The meanings of the terms "nucleotide body", "product", "antibody", "organic compound having affinity for a protein", "biopolymer having affinity for a protein" and the like are as explained above.

A natural nucleotide body or artificial nucleotide body can be used as the analyte. Artificial nucleotide bodies include those that are completely artificial and those that are derived from natural nucleotide bodies. Artificial nucleotide bodies are advantageous in some cases because they allow for increased detection sensitivity and stability.

It is possible to use either a single-stranded nucleotide body or a double-stranded nucleotide body that is a pair of single-stranded nucleotide bodies complementary to one another. A single-stranded nucleotide body is preferred from the standpoint of ease of elongation and contraction, while a double-stranded nucleotide body is often desirable for lying horizontal to or standing up from the substrate electrode. Different nucleotide bodies can also be used for each electrode. The length of the nucleotide chain can be one residue or more. That is, it may be a mononucleotide chain.

A product obtained by limited digestion of a monoclonal antibody with a protease can be used for the analyte. This is useful because it allows the use of binding resulting from reactions such as antigen-antibody reactions, and can also function as a probe molecule binding specifically with a target molecule.

It is desirable to use a monoclonal antibody, monoclonal antibody Fab fragment or (Fab)$_2$ fragment or a fragment derived from a monoclonal antibody Fab fragment or (Fab)$_2$ fragment as the analyte. A fragment derived from a monoclonal antibody Fab fragment or (Fab)$_2$ fragment is a fragment obtained by segmentation of a monoclonal antibody Fab fragment or (Fab)$_2$ fragment, or a derivative thereof.

It is also desirable to use an IgG antibody, an IgG antibody Fab fragment or (Fab)$_2$ fragment, or a fragment derived from a IgG antibody or IgG antibody Fab fragment or (Fab)$_2$ fragment as the analyte. A fragment derived from an IgG antibody Fab fragment or (Fab)$_2$ fragment is a fragment obtained by segmentation of an IgG antibody Fab fragment or (Fab)$_2$ fragment, or a derivative thereof. An aptamer is also desirable. One reason that these are preferred is that in general, detection sensitivity is better with smaller molecular weights.

From the standpoint of ease of binding with the substrate electrode, the analyte should preferably be a polynucleotide having a thiol group (—SH) or disulfide bond (—S—S—), or include a polynucleotide having a thiol group (—SH) or disulfide bond (—S—S—), and DNA or RNA having a terminal thiol group (—SH) or disulfide bond (—S—S—), or a composite thereof with a protein or the like, is especially desirable. The DNA and RNA may be single-stranded or double-stranded.

The size or length of the analyte is not particularly limited and can be selected appropriately according to the object, but when the analyte is a polynucleotide it should preferably be at least 6 nucleotides long.

(Electrodes)

The substrate electrode of the embodiments can be any that is capable of binding with the analyte and whereby the signal obtained from a marker provided on an analyte bound to the substrate electrode can change according to AC voltage applied between the substrate electrode and a counter electrode, as long as the intent of the invention is not violated, and the form thereof is not particularly limited. Any kind of binding can be used in this case as long as the intent of the invention is not violated, such as covalent bond, coordinate bond and other forms of chemical bond as well as biological bond, static electric binding, physical adsorption, chemical adsorption and the like. Chemical bond is preferred from the standpoint of stability of movement of the analyte in response to the external field, a chemical bond including a sulfur atom (S) is preferred from the standpoint of ease of binding and controllability, and specifically binding of S with the substrate electrode by means of a thiol group (—SH), disulfide bond (—S—S—) or the like is preferred.

For example, the substrate electrode of the embodiments can be obtained by providing an electrode on a substrate surface and providing the electrode surface with a structural part capable of binding with the analyte (analyte binding part). The substrate electrode may be single-layered or multi-layered, or may have a non-layered structure.

The material of the substrate in this case is not particularly limited, and desirable examples include glass (such as quartz glass), ceramics, plastics, metals, silicon, silicon oxide, silicon nitride, sapphire and the like. One kind of material may be used, or two or more may be used in combination.

The shape, structure, size and surface properties of the substrate electrode and the number thereof are not particularly limited, and can be selected appropriately according to the object. Examples of shapes include flat plates, circles, ovals and the like. Examples of surface properties include gloss, roughness and the like. The size is not particularly limited, and can be selected appropriately according to the object.

The size, shape and the like of the substrate electrode can be adjusted as desired by coating the surface with an insulating film so that only a part of the substrate electrode is exposed. The number of substrates is not particularly limited and can be selected appropriately according to the object, and either one or two or more can be used.

The material, shape, structure, thickness, size and the like of the insulating film in this case are not particularly limited and can be selected appropriately according to the object, but the material may be a resist material for example. Examples of resist materials include g-line resists, i-line resists, KrF resists, ArF resists, $F_2$ resists, electron beam resists and the like.

The material of the substrate electrode is not particularly limited as long as it is electrically conductive, and can be selected appropriately according to the object. Examples include metals, alloys, conductive resins, carbon compounds and the like. Examples of metals include gold, platinum, silver, copper, zinc and the like. Examples of alloys include alloys of two or more of the metals listed above and the like. Examples of conductive resins include polyacetylene, polythiophene, polypyrrole, poly(p-phenylene), polyphenylenevinylene, polyaniline and the like. Examples of carbon compounds include conductive carbon, conductive diamonds and the like. One of these may be used alone, or two or more may be used in combination. Au and other precious metals are chemically stable and can be used by preference. This facilitates the adsorption of the biopolymer on the substrate electrode when using it as the analyte. Multiple substrate electrodes may also be provided on a substrate.

Figure 2:
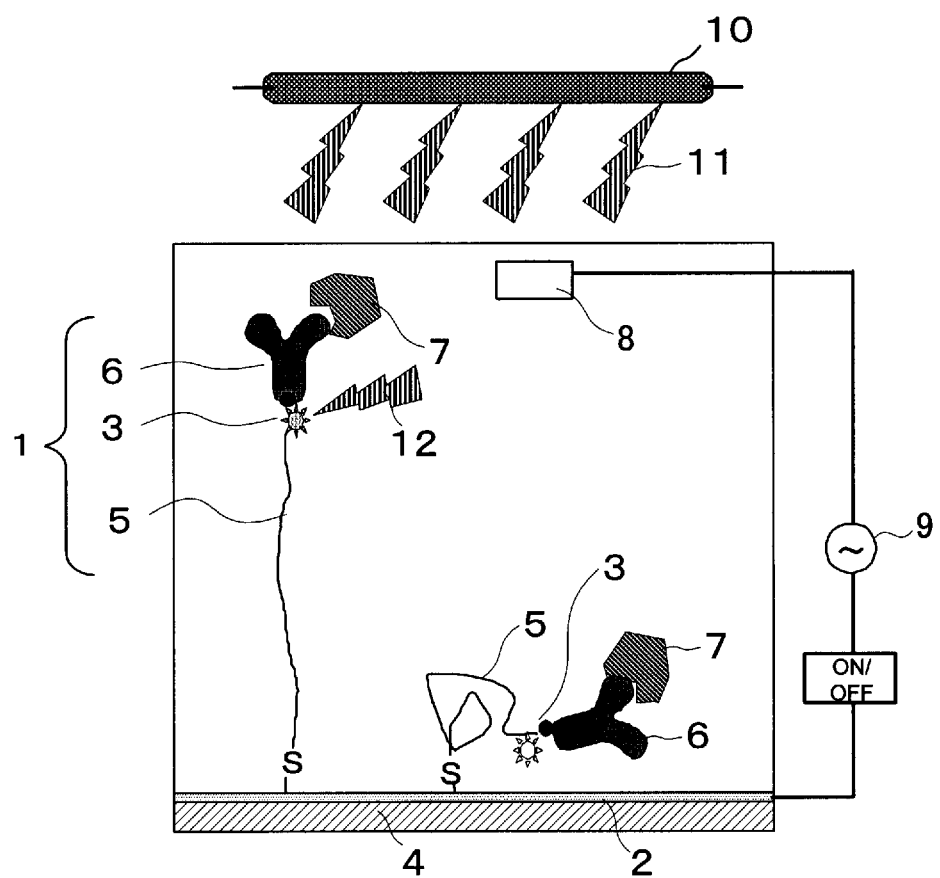
FIG. 2 is a schematic view of an analyte evaluation apparatus showing the behavior of each part of the analyte.

When binding with the analyte is possible without a particular analyte binding part, no analyte binding part need be provided on the surface. An example of an analyte that is a nucleotide body capable of binding to an Au layer via its thiol group is analyte 1 in FIG. 2, which has target molecule 7 bound to a probe molecule having an evaluation object binding part 6, sensing part 5 with a natural single-stranded oligonucleotide structure and marker 3 (part consisting of marker 3, sensing part 5 and evaluation object binding part 6) bound to an Au electrode (substrate electrode 2) on sapphire substrate 4 by reacting the analyte for 24 hours at room temperature with a polished Au electrode. Sensing part 5 is the part having an elongation and contraction function, while evaluation object binding part 6 is the part that binds to the target molecule that is the object of evaluation in this case. If evaluation object binding part 6 has the function of binding specifically to the object of evaluation, the probe molecule will bind specifically to target molecule 7. The S at the bottom of the single-stranded oligonucleotide structure represents binding of the probe molecule to Au electrode 2 via a thiol group. A known metal other than Au can be used for the electrode surface binding with the thiol group. In FIG. 2, a Fab fragment of monoclonal immunoglobulin IgG is fixed to the end of the oligonucleotide chain as evaluation object binding part 6, which has the property of binding specifically to the object of evaluation (target molecule).

The analyte is elongated in the left part of FIG. 2 and contracted in the right part. When in a contracted state, the probe molecule can be made elongated by applying a specific potential difference between Au electrode 2 and counter electrode 8 by means of external electric field applicator 9.

In this case, fluorescence 12 is obtained by exposure to light 11 from light exposure unit 10. In FIG. 2, the object of evaluation is the target molecule bound to the probe molecule. If the probe molecule itself (that is, the analyte before binding with the target molecule) is the object of evaluation, fluorescence emission/quenching is evaluated without binding the target molecule to the probe molecule.

In FIG. 2, the thiol group and marker were introduced into the single-stranded oligonucleotide in advance. The thiol group and marker are preferably introduced at the ends of the single-stranded nucleotide, with the marker preferably introduced at the 3' end if the thiol group is introduced at the 5' end and vice versa. In this case, the oligonucleotide chain was fixed on a round Au electrode 1 mm in diameter.

When an analyte binding part is provided as part of the substrate electrode, the material thereof can be any that can bind with the analyte, and examples include molecules capable of binding with the analyte by chemical binding or intermolecular force. After the analyte binding part has bound to the analyte, the part consisting of the analyte binding part and analyte can be considered as an analyte. If the analyte binding part is capable of elongation and contraction, the analyte before binding with the analyte binding part does not need to have an elongation and contraction function.

In general, binding between the substrate electrode and the analyte should ideally be quantitative, but depending on the type of binding there may be rather a large dissociation constant. If this dissociation constant is too large, binding may gradually decline during washing in a buffer solution for example. For this reason, it is normally desirable that the dissociation constant of binding between the substrate electrode and analyte be $10^{-5}$ or less.

When such a substrate electrode is immersed in an aqueous solution as the medium and an AC field is applied between it and a counter electrode arranged in the aqueous solution, it becomes possible for the analyte to elongate and contract.

When providing the substrate electrode on the substrate, an adhesive layer can be provided between the two to improve adhesiveness between the substrate electrode and the substrate. The material, form, structure, thickness, size and the like of the adhesive layer are not particularly limited and can be selected appropriately according to the object, and examples of materials include chromium and titanium. The structure is not particularly limited and can be selected appropriately according to the object, and may be either a monolayer structure or a layered structure.

The counter electrode of the embodiments is arranged facing the substrate electrode so that potential can be directly applied to both. The form and material of the counter electrode are not particularly limited, and can be selected appropriately from known forms and materials. Examples include platinum wires, platinum plates, platinum coils, gold wires and the like. The number of the counter electrodes is not particularly limited, and there may be more than one.

Instead of a two-electrode system, a three-electrode system using a reference electrode may be adopted for the analyte evaluation apparatus. The reference electrode is an electrode for adjusting the potential difference between the substrate electrode and the counter electrode. The form and material of the reference electrode are not particularly limited, and can be selected appropriately from known forms and materials. Examples include silver-silver chloride (Ag/AgCl), mercury-mercury chloride ($Hg/Hg_2Cl_2$), saturated calomel electrodes and the like. The number of reference electrodes is not particularly limited, and there may be more than one.

(Voltage Application Means, Signal Detection Means)

The voltage application means and signal detection means are not particularly limited and can be selected from known means.

The waveform of the AC voltage supplied by the voltage application means is not particularly limited, but is typically a sine wave or rectangular wave. For the voltage value, the potential value should preferably be adjusted so as not to break the bond between analyte and substrate, and an absolute value of 0.5 V or less is preferred in the case of binding between S and the substrate electrode. The "AC voltage" here may also include DC components. Consequently, the average value may be 0 V, or may be a positive value, or may be a negative value. The frequency of the AC voltage is also not particularly limited, but a frequency range (1 MHz or less) that allows formation of an electrical double layer as a source for the electric field is desirable.

When the signal to be detected is fluorescence, a light-illuminating means is required as an auxiliary means for causing emission and quenching of the fluorescence. Ultraviolet light or visible light corresponding to the fluorescent marker can be used as this light-illuminating means.

When the signal to be detected is redox current, it is desirable to apply AC voltage that alternates around the redox potential of the redox marker, and observe the redox current.

(Marker)

The number of markers in the analyte is not particularly limited and can be selected appropriately according to the object, but there must be at least one and may be two or more. The position of the marker in the analyte is not particularly limited and can be selected appropriately according to the object, but when the analyte is a strand it may be positioned at the end, and when the analyte is a polynucleotide or contains a polynucleotide, it may be at the 3' end or 5' end.

In some cases the marker may be added by covalent bond as part of the object of evaluation, but it may also be added by covalent bond as part of the analyte (probe molecule) before binding with the object of evaluation, or may be contained within the nucleotide body or the like by being intercalated between adjacent complementary bonds for example, or may be incorporated within part of the nucleotide body or the like by substitution. The marker should preferably be located near an end of the analyte.

The marker may be any capable of emitting a signal in response to AC voltage applied between the substrate electrode and counter electrode, as long as the intent of the embodiments is not violated. The signal in this case may include any physical signal, chemical signal or biological signal, but of these, electromagnetic waves and redox current are preferred, and electromagnetic waves or especially a fluorescent marker that emits the fluorescence by the excitation of the effect of light is preferred.

Examples of fluorescent markers include fluorescent dyes, metals, semiconductor nanospheres and the like.

Figure 6:
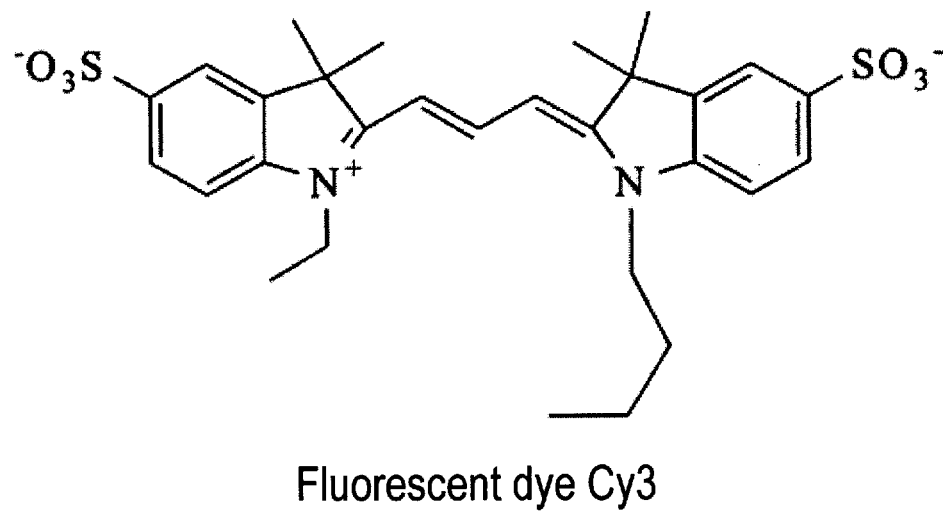
FIG. 6 shows the structure of Cy3 as one example of a fluorescent dye.

When the substrate electrode is of metal, a fluorescent dye that does not emit fluorescence even when exposed to light at an absorbable wavelength as long as it interacts with the metal (for example, when it is positioned near the metal), but which is capable of emitting fluorescence in response to light energy when exposed to light at an absorbable wavelength while it is not interacting with the metal (when separated from the metal for example), is especially preferred as the emitting/quenching part. The fluorescent dye is not particularly limited and can be selected appropriately according to the object from known dyes, but desirable examples include the compounds listed in FIG. 6.

An example of one that can be used by preference as the marker is indocarbocyanine 3 (Cy3®).

Figure 7:
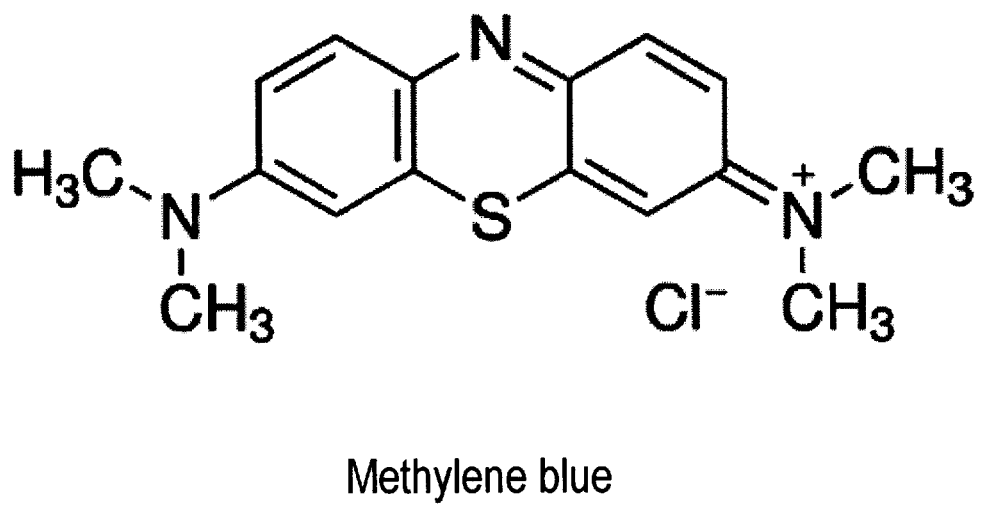
FIG. 7 shows the structure of methylene blue as one example of a redox marker.
Figure 8:
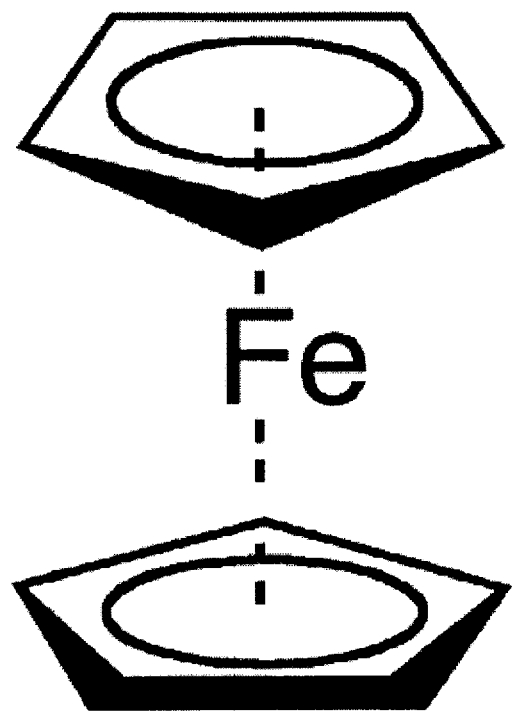
FIG. 8 shows the structure of ferrocene as one example of a redox marker.

When the marker is a redox marker, the signal is redox current. Examples of such redox markers include methylene blue ($C_{16}H_{18}ClN_3S$: FIG. 7) and ferrocene ($C_{10}H_{10}Fe$: FIG. 8).

(Changing Frequency of AC Voltage)

Figure 3:
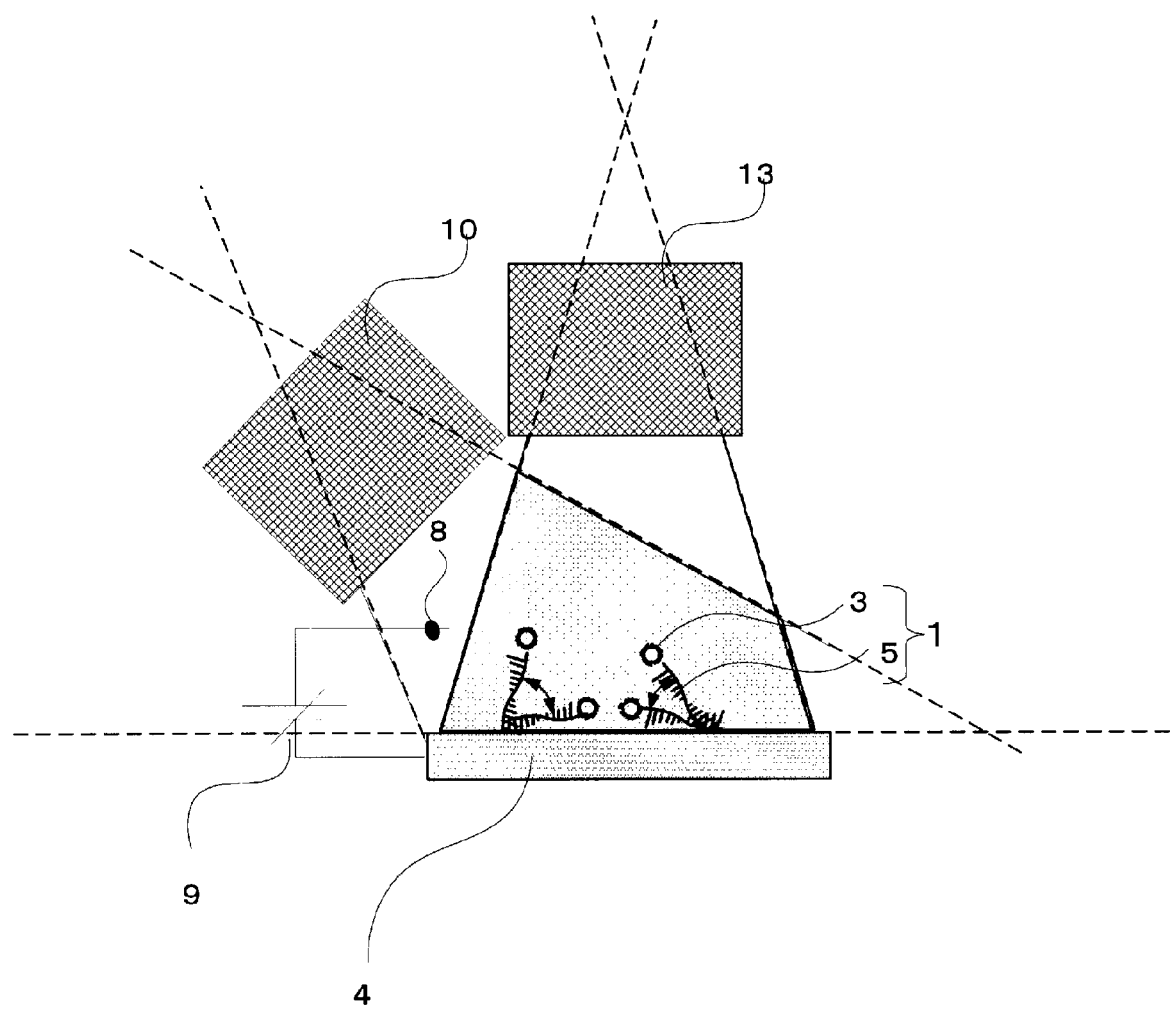
FIG. 3 is a schematic view of the analyte evaluation apparatus used in the examples.

The behavior of the resulting fluorescence signal was observed using the analyte evaluation apparatus of FIG. 3. FIG. 3 shows analyte 1, with a marker, bound to the substrate electrode on substrate 4, with fluorescence excited by light illuminating means 10 being detected by fluorescence detection means 13.

Figure 4:
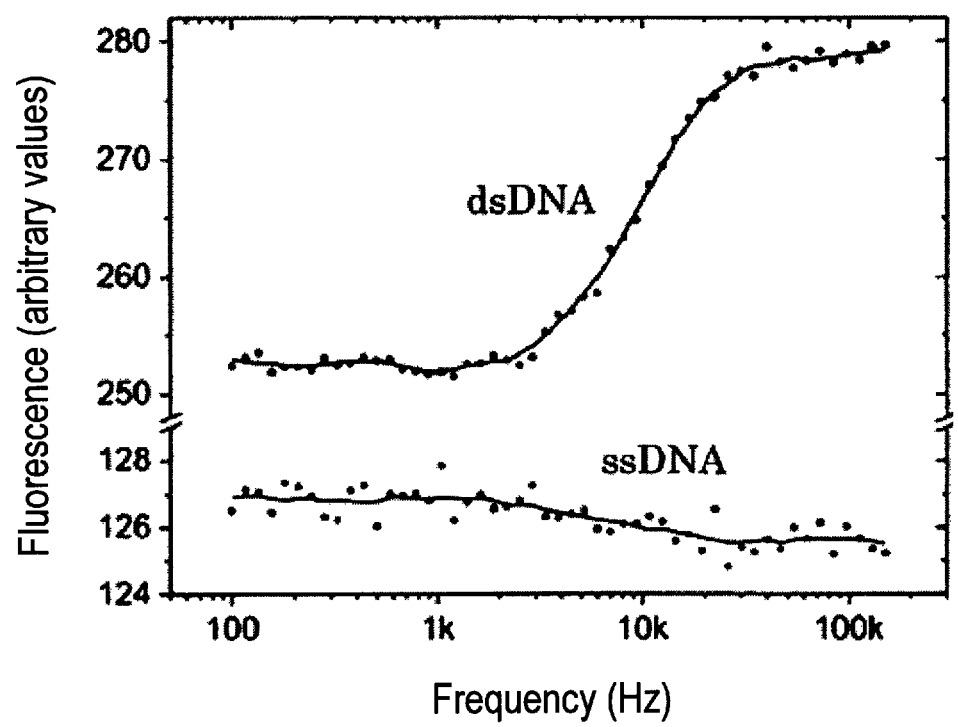
FIG. 4 is a graph showing the behavior of the marker signal in response to changes in the frequency of the AC voltage.

The frequency of the applied voltage was altered under these conditions. The results are shown in FIG. 4. FIG. 4 is a graph showing the status of fluorescence intensity when the frequency was altered while applying sine-wave AC voltage to ssDNA (single-stranded DNA) and dsDNA (double-stranded DNA). The ssDNA in this case corresponds to the probe molecule, while the complement DNA of the dsDNA corresponds to the target molecule. Fluorescence intensity is the average of intensity of fluorescence emitted and quenched due to application of AC voltage.

From FIG. 4, it is clear that while fluorescence intensity declines slightly within the studied range in the case of ssDNA, fluorescence intensity increases dramatically past a certain value in the case of dsDNA. This is thought to occur because the falling time is shorter than the rising time with ssDNA, but conversely the rising time is shorter than the falling time with dsDNA, and consequently falling comes to dominate in the case of ssDNA as the frequency is raised, and the average fluorescence intensity decreases. Conversely, rising comes to dominate in the case of dsDNA, and the average fluorescence intensity increases (see for example U. Rant et al., "Dissimilar kinetic behavior of electrically manipulated single- and double-stranded DNA tethered to a gold surface", Biophysical Journal, 2006, Vol. 90, p. 3666-3671).

From these results, it appears that the signal behavior in response to changes in the applied voltage frequency should also vary according to the type of analyte. Such properties are generally called frequency response.

Consequently, it should be possible to use these frequency response to detect the presence or absence of an object of evaluation or differences in the type of object of evaluation by collecting various separate types of data and observing the resulting signals. The type of an object of evaluation includes differences in molecular weight, differences in form (differences between bulky molecules and non-bulky molecules, differences between linear molecules and branched molecules), differences in flexibility (presence of nicks and snips in dsDNA), differences in charge and the like. Since changes in the behavior of the signal in response to changes in frequency are also affected by the amount of analyte adhering per unit of surface area, it should also be possible to assay the amount of analyte adhering per unit of surface area, or in other words the concentration of the analyte.

The way of changing the frequency is not particularly limited and can be selected appropriately by determining whether useful signal behavior of the marker can be observed. When large changes are anticipated as in the case of the dsDNA in FIG. 4, a single, stepwise change to a different frequency may be sufficient. It is also useful to investigate what signal changes are observed at what frequency by changing the frequency in multiple stages. Moreover, more detailed signal changes can be obtained by varying the frequency continuously.

EXAMPLES

Examples and comparative examples are given next.

Example 1

FIG. 3 shows the configuration of an apparatus necessary for implementing the embodiments. FIG. 3 is a rough explanatory diagram for explaining one example of an apparatus comprising analyte 1 having fluorescent dye (fluorescent label, i.e. marker) 3 in the molecule fixed (bound) to a gold electrode (substrate electrode, not shown) on substrate 4, optical fiber (incident light fiber) 10 whereby the analyte molecule is exposed to light at a wavelength at which the fluorescent dye is excited to cause emission and quenching, and optical fiber (receiving fiber) 13 for detecting emission and quenching from the fluorescent dye.

The gold electrode is connected to an AC power source capable of high-frequency drive with respect to the solution potential and a DC power source for applying offset potential.

Using as the analyte single-stranded DNA (48-base probe DNA; ss-48 mer-probe-DNA) having a thiol group (—SH) at one end and a fluorescent cyanine dye (Cy3) as the fluorescent dye at the other end, this DNA was self-assembled by the methods described in A. Ulman, "Formation and structure of self-assembled monolayers", Chem. Rev., 1996, Vol. 96, No. 4, p. 1533-1554 to thereby fix (bind) it via a sulfur atom to a gold electrode (2 mm dia.) and form a molecular film of this DNA on the gold electrode.

The signal from the fluorescent label was then observed as an AC field (sine wave, E=−0.15±0.25 Vrms) was applied between the gold electrode with the DNA fixed thereon and the counter electrode (platinum electrode). The frequency of the AC field was altered, and the average value (photocounter shutter opened at 1 Hz) of the signal from the fluorescent label was recorded as the analyte was driven with an AC field from a low frequency of 100 Hz to a high frequency of 150 kHz. A buffer solution (Tris 10 mM, NaCl 50 mM, pH 7.3) was used for measurement. The results are plotted in FIG. 4 as ssDNA.

Next, this DNA fixed on the substrate was hybridized specifically with non-labeled complement strand DNA to form double-stranded DNA. As the hybridization conditions, the analyte was kept for 1 hour in a buffer solution (Tris 10 mM, NaCl 200 mM, pH 7.3) containing 1 µM of complement strand DNA and washed with a buffer solution (Tris 10 mM, NaCl 50 mM, pH 7.3) containing no complement strand DNA, and the signal from the fluorescent label (fluorescent dye) was recorded with the frequency of the AC field altered as in the aforementioned measurement method. The results are plotted as dsDNA in FIG. 4. It is clear from FIG. 4 that ssDNA and dsDNA behave completely differently at high frequencies.

When complement strand DNA is the target molecule to be evaluated, the presence or absence of the target molecule in the evaluated solution can be detected by observing the driving frequency response of the signal from the fluorescent label. The target molecule does not need to be labeled in this case.

One advantage is that because the signal from the fluorescent label is a unique signal reflecting the physical properties of the ssDNA or dsDNA molecule, it is possible to evaluate the target while avoiding the influence of other coexisting contaminants as well as mis-detection of non-specifically adsorbed target and the like, resulting in high selectivity and low noise.

In this example, any frequency that is sufficiently lower than the value of the driving frequency can be used as the average value of the signal from the fluorescent label, or the signal may be recorded continuously (DC). Moreover, the driving frequency response of the DNA are measured in detail from 100 Hz to 150 kHz, but as is shown in FIG. 4, the target molecule can also be evaluated by observing the frequency at any two or more points with significant differences. When changes in the signal before and after binding of the target molecule can be predicted, or when the changes are already known from preliminary testing, the signal does not need to be evaluated before and after binding, and the presence or absence of the target molecule can be evaluated by evaluating only the signal after the test, corresponding to binding of the target molecule.

In this example the analyte is ssDNA and the target molecule is its complement strand DNA, but of course any can be used as long as there is a difference between the driving frequency response of the analyte and the analyte bound to the target molecule.

Example 2

FIG. 2 shows the configuration of an apparatus necessary for implementing the embodiments. FIG. 2 is a rough explanatory diagram for explaining one example of an apparatus comprising analyte 1 having in the molecule fluorescent dye (fluorescent label, i.e. marker) 3 and probe molecule 6 (which binds specifically to target molecule 7) fixed (bound) to gold electrode 2 on substrate 4, optical fiber (incident light fiber) 10 whereby the analyte molecule is exposed to light at a wavelength at which the fluorescent dye is excited, causing emission and quenching, and an optical fiber (light-receiving fiber, not shown) for detecting emission and quenching from the fluorescent dye.

The gold electrode is connected to an AC power source capable of high-frequency driving with respect to the solution potential and a DC power source for applying offset potential.

Figure 9:
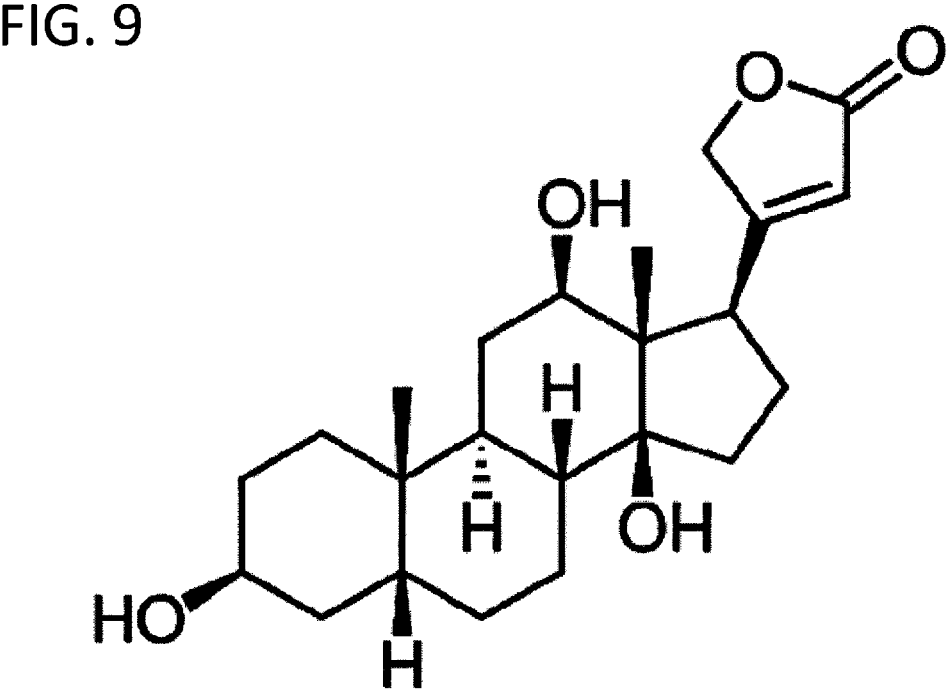
FIG. 9 shows the structure of the digoxigenin described in Example 2.

Using as the analyte single-stranded DNA (48-base probe DNA; ss-48 mer-probe-DNA) having a thiol group (—SH) at one end and a fluorescent cyanine dye (Cy3) as the fluorescent dye at the other end, this DNA was self-assembled by the methods described in A. Ulman, "Formation and structure of self-assembled monolayers", Chem. Rev., 1996, Vol. 96, No. 4, p. 1533-1554 to thereby fix (bind) it via a sulfur atom to a gold electrode (2 mm dia.) and form a molecular film of this DNA on the gold electrode. This DNA fixed on the substrate was then hybridized with complement strand DNA having at one end a probe molecule (digoxigenin; see FIG. 9) that binds specifically to a target molecule (anti-digoxigenin; AntiDig) to form double-stranded DNA. As the hybridization conditions, the analyte was kept for 1 hour in a buffer solution (Tris 10 mM, NaCl 200 mM, pH 7.3) containing 1 µM of complement strand DNA and then washed in a buffer solution (Tris 10 mM, NaCl 50 mM, pH 7.3) containing no complement strand DNA to form double-stranded DNA comprising the fluorescent dye and probe molecule on the substrate.

Figure 5:
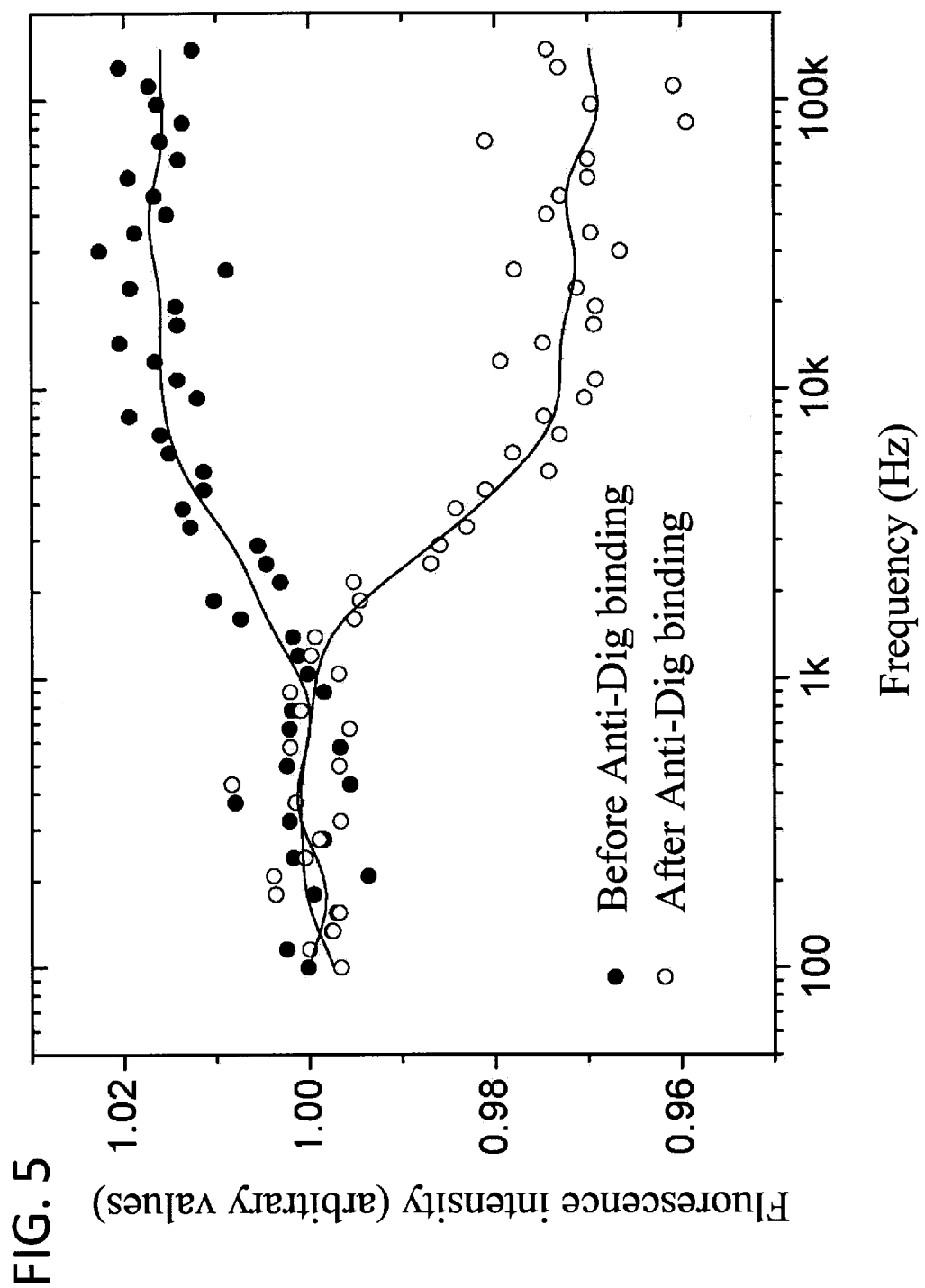
FIG. 5 is a graph showing the behavior of the marker signal in response to changes in the frequency of the AC voltage in Example 2.

The signal from the fluorescent label was then observed as an AC field (sine wave, E=−0.15±0.25 Vrms) was applied between the gold electrode with the DNA fixed thereon and the counter electrode (platinum electrode). The frequency of the AC field was altered, and the average value of the signal from the fluorescent label was recorded as the analyte was driven with an AC field from a low frequency of 100 Hz to a high frequency of 150 kHz. The photocounter shutter was opened at 1 Hz. A buffer solution (Tris 10 mM, NaCl 50 mM, pH 7.3) was used for measurement. The results are plotted in FIG. 5 as "before AntiDig binding".

Next, this double-stranded DNA fixed on the substrate was bound as a probe molecule to a target molecule. As the binding conditions, the analyte was kept for 1 hour in a buffer solution (Tris 10 mM, NaCl 200 mM, pH 7.3) containing 50 nM of the target molecule and washed with a buffer solution (Tris 10 mM, NaCl 50 mM, pH 7.3) containing no target molecule, and the signal from the fluorescent label (fluorescent dye) was recorded with the frequency of the AC field varied as in the aforementioned measurement method. The results are plotted as "after AntiDig binding" in FIG. 5. It is clear from FIG. 5 that completely different behaviors occur at high frequencies before and after binding with the target.

It is thus possible to detect the presence or absence of a target molecule in a target solution by observing the driving frequency response of a signal from a fluorescent label. In this case, the target molecule does not need to be labeled.

Since the signal from the fluorescent label is a unique signal reflecting the physical properties of the molecule before and after binding with the target, it is possible to evaluate the target while avoiding the influence of other coexisting contaminants as well as mis-detection of non-specifically adsorbed target and the like, resulting in high selectivity and low noise.

In this example, any frequency that is sufficiently lower than the value of the driving frequency can be used as the average value of the signal from the fluorescent label, or recording may be continuous (DC). Also, the DNA driving frequency response are measured continuously in detail from 100 Hz to 150 kHz, but it is clear from FIG. 4 that the target molecule could be evaluated by observing any two or more frequencies that are significantly different. When the difference in the signal before and after binding with the target molecule can be predicted in advance, or when the difference is known from preliminary testing, the signal does not need to be evaluated before and after binding, and instead it is possible to evaluate only the post-test signal (corresponding to binding with the target molecule) to evaluate the presence or absence of the target molecule.

Moreover, in this example the sample is digoxigenin-DNA and the target molecule is anti-digoxigenin, but of course any could be used as long as there is a difference in driving frequency response between the analyte and the analyte bound to the target molecule.

What is claimed is:

1. An analyte evaluation method comprising: applying AC voltage between a substrate electrode on a substrate and a counter electrode; and
   evaluating the analyte by observing an behavior of a signal obtained from a marker provided on the analyte bound to the substrate electrode,
   wherein a frequency of the AC voltage is varied during the applying the AC voltage,
   wherein the marker is a fluorescent marker, and the signal is emission and quenching of the fluorescent marker, and
   wherein the signal is obtained from the fluorescent marker at a constant frequency lower than the frequency of the AC voltage, and
   wherein the evaluation comprises at least one of differences in molecular weight, differences in form including differences between bulky molecules and non-bulky molecules, and differences between linear molecules and branched molecules, differences in flexibility, and differences in charge.

2. The analyte evaluation method according to claim 1, wherein the analyte comprises a probe molecule comprising the marker and a target molecule binding specifically to the probe molecule.

3. The analyte evaluation method according to claim 1, wherein the change in the frequency is a stepwise change to at least one different frequency.

4. The analyte evaluation method according to claim 1, wherein the change in the frequency is a continuous change.

5. The analyte evaluation method according to claim 1, comprising a stepwise or continuous altering of the voltage value of the AC voltage.

6. The analyte evaluation method according to claim 1, wherein a waveform of the AC voltage is a sine wave or rectangular wave.

7. The analyte evaluation method according to claim 2, wherein another observation is carried out in advance with respect to different target molecules bound to the analyte respectively, and the analyte is evaluated based on a comparison thereof.

8. The analyte evaluation method according to claim 1, wherein the analyte can be positively or negatively charged.

9. The analyte evaluation method according to claim 1, wherein a distance between the marker and the substrate electrode is changed by means of application of the AC voltage.

10. The analyte evaluation method according to claim 1, wherein the analyte includes at least one substance selected from the group consisting of proteins, DNA, RNA, antibodies, natural or artificial single-stranded nucleotide bodies, natural or artificial double-stranded nucleotide bodies, aptamers, products obtained by limited digestion of antibodies with proteases, organic compounds having affinity for proteins, biopolymers having affinity for proteins, complexes thereof, positively or negatively charged ionic polymers, and any combinations thereof.

11. The analyte evaluation method according to claim 10, wherein the analyte includes a natural or artificial single-stranded nucleotide, or a natural or artificial double-stranded nucleotide.

12. The analyte evaluation method according to claim 10, wherein the analyte includes an antibody Fab fragment, or (Fab)$_2$ fragment.

13. The analyte evaluation method according to claim 10, wherein the analyte includes a fragment derived from an IgG antibody, or IgG antibody Fab fragment, or (Fab)$_2$ fragment.

14. The analyte evaluation method according to claim 10, wherein the analyte includes an aptamer.

15. The analyte evaluation method according to claim 1, wherein the target molecule is a protein, DNA, RNA or an antibody.

16. The analyte evaluation method according to claim 1, wherein the signal is obtained at a frequency lower than the driving frequency or at a continuous recording.

* * * * *